United States Patent [19]

Mihm et al.

[11] Patent Number: 5,026,699
[45] Date of Patent: Jun. 25, 1991

[54] USE OF 5,11-DIHYDRO-6H-PYRIDO[2,3-B][1,4]-BENZODIAZEPIN-6-ONES SUBSTITUTED IN THE 11-POSITION FOR TREATING BRADYCARDIA AND BRADYARRHYTHMIA IN HUMAN AND VETERINARY MEDICINE

[75] Inventors: Gerhard Mihm; Wolfgang Eberlein; Welfhard Engel, all of Biberach; Günter Trummlitz, Warthausen; Norbert Mayer, Biberach; Henri Doods, Warthausen; Rudolf Hammer, Ingelheim am Rhein, all of Fed. Rep. of Germany

[73] Assignee: Dr. Karl Thomae GmbH, Biberach an der Riss, Fed. Rep. of Germany

[21] Appl. No.: 367,397

[22] Filed: Jun. 15, 1989

[30] Foreign Application Priority Data

Jun. 15, 1988 [DE] Fed. Rep. of Germany ....... 3820347

[51] Int. Cl.$^5$ ............................................. A61K 31/55
[52] U.S. Cl. .................................................... 514/220
[58] Field of Search ........................................ 514/220

[56] References Cited

U.S. PATENT DOCUMENTS

| | | | |
|---|---|---|---|
| 3,660,380 | 5/1972 | Schmidt et al. | 514/850 |
| 4,210,648 | 7/1980 | Schmidt et al. | 514/220 |
| 4,424,222 | 1/1984 | Engel et al. | 514/220 |
| 4,550,107 | 10/1985 | Engel et al. | 514/220 |
| 4,873,236 | 10/1989 | Engel et al. | 514/220 |

FOREIGN PATENT DOCUMENTS

| | | |
|---|---|---|
| 125607 | 11/1984 | European Pat. Off. . |
| 126336 | 11/1984 | European Pat. Off. . |
| 156191 | 3/1985 | European Pat. Off. . |
| 213293 | 6/1986 | European Pat. Off. . |
| 312895 | 10/1988 | European Pat. Off. . |
| 2821813 | 11/1979 | Fed. Rep. of Germany . |

OTHER PUBLICATIONS

Thomas, Chem. Abs., vol. 90, No. 17, entry #137875s (1979).

Primary Examiner—Mark L. Berch
Assistant Examiner—E. C. Ward
Attorney, Agent, or Firm—D. E. Frankhouser; M-E. M. Timbers; A. R. Stempel

[57] ABSTRACT 5,11-Dihydro-6H-pyrido[2,3-b][1,4]-benzo-diazepinones substituted in the 11-position corresponding to general formula I

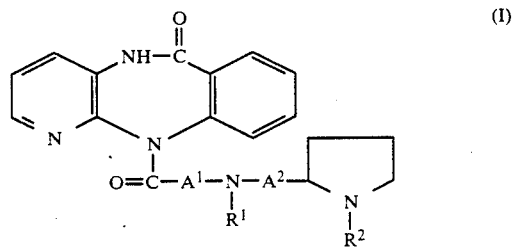

wherein $R^1$ and $R^2$ represent hydrogen atoms or alkyl groups having 1 to 3 carbon atoms, $A^1$ is a straight-chained or branched alkylene group with 1 to 5 carbon atoms, $A^2$ is a methylene group or, if $R^1$ is hydrogen and $R^2$ is methyl, $A^2$ may also be an ethylene group, and the physiologically acceptable acid addition salts thereof are suitable for treating bradycardia and bradyarrhythmia and spasm in the colon, bladder and bronchi.

3 Claims, No Drawings

USE OF 5,11-DIHYDRO-6H-PYRIDO[2,3-B][1,4]-BENZODIAZEPIN-6-ONES SUBSTITUTED IN THE 11-POSITION FOR TREATING BRADYCARDIA AND BRADYARRHYTHMIA IN HUMAN AND VETERINARY MEDICINE

The invention relates to the use of 5,11-dihydro-6H-pyrido[2,3-b][1,4]benzodiazepin-6-ones of general formula I

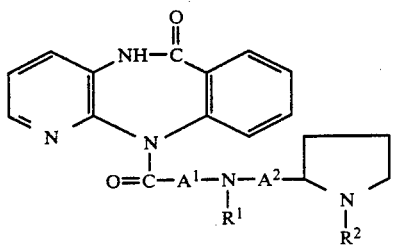

for treating bradycardia and bradyarrhythmia in human and veterinary medicine.

In general formula I $R^1$ and $R^2$, which may be identical or different, represent hydrogen atoms or alkyl groups having 1 to 3 carbon atoms, $A^1$ is a straight-chained or branched alkylene group having 1 to 5 carbon atoms, $A^2$ is a methylene group or, if $R^1$ is hydrogen and $R^2$ is methyl, $A^2$ may also be an ethylene group.

Some of the compounds of general formula I above have been described in DE-C-2 724 478 (corresponding to U.S. Pat. No. 4,210,648 or GB-B-1 581 500) as antiulcerative compounds and compounds which have an inhibitory effect on the secretion of gastric juices, and various methods of preparing them have also been described. The other compounds of general formula I can be prepared analogously thereto.

It has been found, surprisingly, that the compounds of general formula I and the acid addition salts thereof, but particularly the compounds A=5,11-dihydro-11-[[[2-(1-methyl-2-pyrrolidinyl)ethyl]amino]acetyl]-6H-pyrido[2,3-B]-[1,4]benzodiazepin-6-one and B=5,11-dihydro-11-[[[(1-ethyl-2-pyrrolidinyl)methyl]methylamino]acetyl]-6H-pyrido[2,3-b][1,4]benzodiazepin-6-one and the acid addition salts thereof have favorable effects on heart rate and, in view of their relatively slight mydriatic, salivation-inhibiting and gastric acid secretion-inhibiting effects, they are suitable for use as vagal pacemakers for the treatment of bradycardia and bradyarrhythmia in human and veterinary medicine. Some compounds also show spasmolytic effects on peripheral organs, particularly the colon, bladder and bronchi.

A favorable relation between tachycardiac effects on the one hand and on the other hand the undesirable effects on pupil size and the secretion of tears, saliva and gastric acid which occur in therapeutic agents with an anticholinergic component is of particular importance in the therapeutic use of the substances. The following tests show that the compounds according to the invention exhibit surprisingly good relations of this kind.

A. Studies of binding to muscarinic receptors

In vitro measurement of the $IC_{50}$ value

The organs were donated by male Sprague-Dawley rats weighing 180–220 g. After the heart and submandular gland and cerebral cortex had been removed, all other steps were carried out in ice cold Hepes HCl buffer (pH 7.4; 100 millimolar NaCl, 10 millimolar $MgCl_2$). The whole heart was cut up with scissors. All the organs were then homogenized in a Potter apparatus.

For the binding test the homogenized organs were diluted as follows:

| | |
|---|---|
| Whole heart | 1:400 |
| Cerebral cortex | 1:3000 |
| Submandibular gland | 1:400 |

The homogenized organs were incubated at a certain concentration of the radioligand and at a series of concentrations of the non-radioactive test substances in an Eppendorf centrifuge tube at 30° C. Incubation lasted 45 minutes. The radioligand used was 0.3 nanomolar $^3H$—N- methylscopolamine ($^3H$-NMS). Incubation was ended by the addition of ice cold buffer followed by vacuum filtration. The filters were rinsed with cold buffer and their radioactivity was determined. It represents the sum of specific and non-specific binding of $^3H$-NMS. The proportion of non-specific binding was defined as the radioactivity which was bound in the presence of 1 micromolar quinuclidinylbenzylate. Each measurement was taken four times. The $IC_{50}$ values of the non-labelled test substances were determined graphically. They represent that concentration of test substance at which the specific binding of $^3H$-NMS to the muscarinic receptors in the various organs was inhibited by 50%. The results can be seen from Table I.

B. Investigation of functional selectivity of the antimuscarinic effect

Substances with antimuscarinic properties inhibit the effects of agonists supplied exogenically or of acetylcholine, which is released from cholinergic nerve endings. The following is a description of some methods that are suitable for the detection of cardioselective antimuscarinic agents.

"In vivo" methods

The objective of the methods was to confirm the selectivity of the antimuscarinic effect. Those substances which had been selected on the basis of "in vitro" tests were tested for their 1. $M_1/M_2$ selectivity in the rat,
2. Salivation-inhibiting effect on the rat and
3. Inhibition of the acetylcholine effect on the bladder, bronchi and heart rate in the guinea pig.

1. $M_1/M_2$ selectivity in the rat

The method used was described by Hammer and Giachetti (Life Sciences 31, 2991–2998 (1982)). Five minutes after the intravenous injection of increasing doses of the substance, either the right vagus was electrically stimulated (frequency: 25 Hz; pulse width: 2ms; duration of stimulus: 30s, voltage: supramaximal) or 0.3 mg/kg of McN-A-343 were intravenously injected into male THOM rats. The bradycardia caused by vagus stimulation and the rise in blood pressure caused by McN-A-343 were determined. The dosage of the substances which reduced either the vagal bradycardia (M2) or the rise in blood pressure (M1) by 50% was determined graphically. For the results see Table II.

2. Salivation-inhibiting effect in the rat

Using the method of Lavy and Mulder (Arch. Int. Pharmacodyn 178, 437–445, (1969)) male THOM rats anesthetized with 1.2 g/kg of urethane were given increasing doses of the substance by i.v. route. The secretion of saliva was initiated by subcutaneous administration of 2 mg/kg of pilocarpine. The saliva was absorbed with blotting paper and the surface area covered was measured every 5 minutes by planimetry. The dosage of the substance which reduced the volume of saliva by 50% was determined graphically. For the results see Table II.

3. Inhibition of the effect of acetylcholine on the bladder, bronchi and heart rate in guinea pigs 5 minutes after the administration of the test substance, 10 microgram/kg of acetylcholine were simultaneously injected intravenously and intra-arterially into anesthetized guinea pigs. The heart rate was recorded directly by extracorporeal derivation of the ECG, the expiration resistance according to Konzett-Rössler and contraction of the exposed bladder. In order to determine the inhibition of the acetylcholine activity on the organs under investigation, dosage/activity curves were recorded and from them $-\log ED_{50}$ values were determined. For the results see Table III.

The following compounds, by way of example, were investigated according to the procedures set forth above:

A = 5,11-dihydro-11-[[[2-(1-methyl-2-pyrrolidinyl)ethyl]amino]acetyl]-6H-pyrido[2,3-b][1,4]benzodiazepin-6-one B = 5,11-dihydro-11-[[[(1-ethyl-2-pyrrolidinyl)methyl]methylamino]acetyl]-6H-pyrido[2,3-b][1,4]benzodiazepin-6-one and as comparison substances C = 11-[[2-[(diethylamino)methyl]-1-piperidinyl]acetyl]-5,11-dihydro-6H-pyrido[2,3-b][1,4]benzodiazepin-6-one (see U.S. Pat. No. 4,550,107)

D = 5,11-dihydro-11-[(4-methyl-1-piperazinyl)acetyl]-6H-pyrido[2,3-b][1,4]benzodiaze-6-one (pirenzepine, see U.S. Pat. No. 3,660,380) and E = atropine.

TABLE I

| Receptor Binding Tests in vitro: Results: | | | |
|---|---|---|---|
| Receptor Binding Tests IC$_{50}$ [nmol l$^{-1}$] | | | |
| Substance | Cortex | Heart | Submandibular gland |
| A | 100 | 15 | 150 |
| B | 30 | 6 | 50 |
| C | 1200 | 140 | 5000 |
| D | 100 | 1500 | 200 |
| E | 2 | 4 | 4 |

The information shown in Table I above shows that the new compounds of general formula I distinguish between muscarinic receptors in different tissues. This is clear from the substantially lower IC$_{50}$ values when the test substances are investigated on preparations from the heart compared with those from the cerebral cortex and submandibular gland.

TABLE II

| M$_1$/M$_2$ selectivity and salivation-inhibiting activity on the rat: Results: | | | |
|---|---|---|---|
| $-\log ED_{50}$ [mol kg$^{-1}$] | | | |
| Substance | Heart | Blood pressure | Salivation inhibition |
| A | | | |
| B | 8.13 | 6.85 | 6.09 |
| C | 6.42 | 5.63 | 5.00 |
| D | 5.60 | 6.94 | 6.22 |
| E | 7.94 | 7.34 | 7.60 |

TABLE III

| Inhibition of acetylcholine activity on the bladder, bronchi and heart rate in the guinea pig: Results: | | | |
|---|---|---|---|
| $-\log ED_{50}$ [mol kg$^{-1}$] | | | |
| Substance | Heart | Bronchi | Bladder |
| A | 7.01 | 6.99 | 6.27 |
| B | 7.34 | 7.46 | 5.93 |
| C | 5.84 | 5.58 | 4.73 |
| D | 5.85 | 6.57 | 5.36 |
| E | 7.70 | 7.96 | 7.03 |

The pharmacological data in Tables II and III above show - in total agreement with the receptor binding studies - that the heart rate is increased by the above-mentioned compounds even at dosages at which there is no restriction in the secretion of saliva.

Moreover, the pharmacological data in Table III above indicate a surprisingly high power of distinction between the heart and smooth muscle.

The above-mentioned substances show a substantially improved effectiveness compared with the known compound C. At the same time, their therapeutically useful selectivity is retained. This results in a reduction in the quantity of drug to be administered to the patient without increasing the risk o muscarinic side-effects.

Furthermore, the compounds prepared according to the invention are well tolerated; even in the highest doses administered, no toxic side-effects were observed in the pharmacological trials.

The active substances or their physiologically acceptable salts may be incorporated in known manner in the usual pharmaceutical preparations, e.g. in solutions, suppositories, plain or coated tablets, capsules or infusions. The daily dosage is generally between 0.002 and 5 mg/kg, preferably 0.05 and 1.0 mg/kg of body weight, optionally administered in the form of several, staggered individual doses in order to achieve the desired therapeutic effect.

The active substances may also be converted into the physiologically acceptable salts thereof using corresponding inorganic or organic acids. Acids which have proved suitable include, for example, hydrochloric, hydrobromic, sulphuric, phosphoric, tartaric, fumaric, citric, maleic, succinic and malic acid.

The following Examples illustrate the preparation of some pharmaceutical administration forms:

EXAMPLE I

Tablets containing 50 mg of 5,11-dihydro-11-[[[2-(1-methyl-2-pyrrolidinyl)ethyl]amino]acetyl]-6H-pyrido[2,3-b][1,4]benzodiazepin-6-one

| Composition: | |
|---|---|
| 1 tablet contains: | |
| Active substance | 50.0 mg |
| Lactose | 148.0 mg |
| Potato starch | 65.0 mg |
| Magnesium stearate | 2.0 mg |
| | 265.0 mg |

Method of preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.

| Weight of tablet: | 220 mg |
|---|---|
| Punch: | 9 mm |

EXAMPLE II

Coated tablets containing 50 mg of 5,11-dihydro-11-[[[2-(1-methyl-2-pyrrolidinyl)ethyl]amino]acetyl]-6H-pyrido[2,3-b][1,4]benzodiazepin-6-one The tablets prepared according to Example I are coated, by a known method, with a coating consisting essentially of sugar and talc. The finished coated tablets are polished with beeswax.
Weight of coated tablet: 300 mg

EXAMPLE III

Ampoules containing 10 mg of 5,11-dihydro-11-[[[2-(1-methyl-2-pyrrolidinyl)ethyl]amino]acetyl-6H-pyrido[2,3-b][1,4]benzodiazepin-6-one dihydrochloride

| Composition: | |
|---|---|
| 1 ampoule contains: | |
| Active substance | 10.0 mg |
| Sodium chloride | 8.0 mg |
| Distilled water | ad 1 ml |

Method of preparation

The active substance and sodium chloride are dissolved in distilled water and then made up to the volume specified. The solution is sterile filtered and transferred into 1 ml ampoules.
Sterilization: 20 minutes at 120° C.

EXAMPLE IV

Suppositories containing 50 mg of 5,11-dihydro-11-[[[(1-ethyl-2-pyrrolidinyl)methyl]methylamino]acetyl]-6H-pyrido[2,3-b][1,4]benzodiazepin-6-one

| Composition: | | |
|---|---|---|
| 1 suppository contains: | | |
| Active substance (e.g. Witepsol W 45$^{(R)}$) | 1 | 50.0 mg |
| | 1 | 695.0 mg |
| | | 745.0 mg |

Method of preparation

The finely powdered active substance is suspended in the molten suppository mass which has been cooled to 40° C. The mass is poured at 37° C. into slightly chilled suppository moulds.
Weight of suppository: 1.745 g

EXAMPLE V

Drops containing 5,11-dihydro-11-[[[(1-ethyl-2-pyrrolidinyl)methyl]methylamino]acetyl]-6H-pyrido[2,3-b][1,4]benzodiazepin-6-one dihydrochloride

| Composition: | |
|---|---|
| 100 ml of drops solution contain: | |
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 5.0 g |
| Sodium cyclamate | 1.0 g |
| Glycerol | 15.0 g |
| Distilled water | ad 100.0 ml |

Method of preparation

The active substance and sodium cyclamate are dissolved in about 70 ml of water and glycerol is added. The p-hydroxybenzoates, aniseed oil and menthol are dissolved in ethanol and this solution is added with stirring to the aqueous solution. Finally, the solution is made up to 100 ml with water and filtered to remove any suspended particles.

What is claimed is:

1. A method for treating bradycardia and bradyarrhythmia in a warm-blooded animal which comprises administering to said animal a therapeutically effective amount of an 11-substituted 5,11-dihydro-6H-pyrido-[2,3-b][1,4]benzodiazepin-6-ones of general formula I

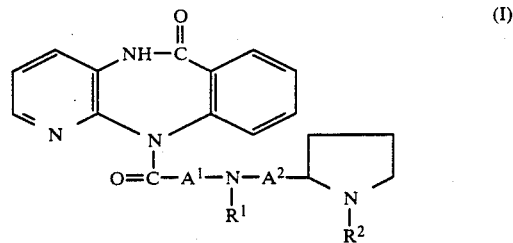

wherein $R^1$ and $R^2$, which may be identical or different, are hydrogen atoms or alkyl groups having 1 to 3 carbon atoms and $A^1$ is a straight-chained or branched alkylene group having 1 to 5 carbon atoms, $A^2$ is a methylene group or, if $R^1$ is hydrogen and $R^2$ is methyl, $A^2$ is a methylene or ethylene group, or the physiologically acceptable acid addition salt thereof.

2. The method as recited in claim 1 wherein the 11-substituted 5,11-dihydro-6H-pyrido-[2,3-b][1,4]benzodiazepin-6-one is 5,11-dihydro-11-[[[2-(1-methyl-2-pyrrolidinyl)ethyl]amino]acetyl]-6H-pyrido[2,3-b][1,4]benzodiazepin-6-one or the physiologically acceptable acid addition salt thereof.

3. The method as recited in claim 1 wherein the 11-substituted 5,11-dihydro-6H-pyrido-[2,3-b][1,4]benzodiazepin-6-one is 5,11-dihydro-11-[[[(1-ethyl-2-pyrrolidinyl)-methyl]methylamino]acetyl]-6H-pyrido[2,3 [1,4]- benzodiazepin-6-one or the physiologically acceptable acid addition salt thereof.

* * * * *